(12) United States Patent
Farrell et al.

(10) Patent No.: US 6,846,787 B1
(45) Date of Patent: Jan. 25, 2005

(54) FATTY ACID SOAP/FATTY ACID BARS WHICH PROCESS AND HAVE GOOD LATHER

(75) Inventors: Terence James Farrell, Tenafly, NJ (US); Charles Craig Nunn, Rutherford, NJ (US)

(73) Assignee: Unilever Home & Personal Care USA Division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/756,616

(22) Filed: Jan. 13, 2004

(51) Int. Cl.$^7$ .............................................. A61K 7/50
(52) U.S. Cl. ........................ 510/152; 510/153; 510/155
(58) Field of Search ............................. 510/141, 152, 510/153, 155

(56) References Cited

U.S. PATENT DOCUMENTS

| | | | |
|---|---|---|---|
| 5,262,079 A | 11/1993 | Kacher et al. | |
| 5,387,362 A | 2/1995 | Tollens et al. | |
| 5,656,579 A | * 8/1997 | Chambers et al. | 510/152 |
| 6,121,216 A | 9/2000 | Narath et al. | |
| 6,242,399 B1 | * 6/2001 | Chambers et al. | 510/154 |

* cited by examiner

Primary Examiner—Necholus Ogden
(74) Attorney, Agent, or Firm—Ronald A. Koatz

(57) ABSTRACT

The invention relates to bar compositions which are structured in such manner (i.e., through specific ternary system) that bars can extrude well and have good properties (e.g., lather), even at low synthetic surfactant level.

6 Claims, 1 Drawing Sheet

All values represented on this diagram are in mol %. The "X" on the caustic axis can for example represent either sodium or potassium. Representing caustic in the manner allows for water to be considered on the tertiary axis when preparing the soap base.

All values represented on this diagram are in mol %. The "X" on the caustic axis can for example represent either sodium or potassium. Representing caustic in the manner allows for water to be considered on the tertiary axis when preparing the soap base.

FATTY ACID SOAP/FATTY ACID BARS WHICH PROCESS AND HAVE GOOD LATHER

FIELD OF THE INVENTION

The invention relates to predominantly fatty acid soap/free fatty acid bars (i.e., having fatty acid soap and/or fatty acid as base) comprising low levels of synthetic surfactant. Specifically, it relates to bars which can have very high levels of soap and/or high levels of free fatty acid and which, because of these high levels, one skilled in the art would not previously have believed could process and/or foam well. However, by using a "pure" fatty acid/pure soap stock (i.e., stock with no more than certain amounts of unsaturates and substantially free of lower chain length fatty acids or fatty acid soaps) to make a precursor bar composition before combining with synthetic and other bar components, unexpectedly it is found possible to provide such bars which process and lather well.

BACKGROUND OF THE INVENTION

While fatty acid soap is known to be an efficient, inexpensive cleansing product, it can also be harsh (e.g., non-mild) to the skin. The short chain (e.g., $C_{14}$ and below, primarily $C_{12}$ and below) and unsaturated long chain (e.g., sodium oleate) soaps, for example, provide good lather and detergency, but can also be harsh and drying.

Applicants have noted that removal of the generally more soluble, harsher components noted above from a soap chain distribution do not generally affect the structuring and the processing properties of a bar (which properties are more dependent on the less harsh, insoluble, longer chain soaps), but could affect, for example, lather properties.

One major challenge, therefore, is to find a bar which is made from fatty acid soap stock (it should be noted that unsaturated, more soluble soaps such as, for example, oleate, generally are derived from the same source as longer chain, insoluble soaps, i.e., from non-nut oils such as tallow or palm) which stock can be used to make bars which process well, retain good foam properties and which have desirable mildness properties.

Applicants have now found it is possible to create a precursor bar formulation from fatty acids and/or fatty acid soaps having no more than a certain mol % unsaturated chain length components and, of the remaining mol % saturated components, substantially no component of chain length $C_{14}$ or below (except for residual or artifact components which are extremely difficult to eliminate from the added synthetic surfactant altogether; these may comprise less than about 1% preferably less than 0.5% of the stock and are preferably absent and, in any event, would result in more than 1% of any $C_{14}$ or below fatty acid or soap components in the final bar).

The precursor bar, which acts as a kind of matrix for additional components to be blended or mixed into the final bar, can be formed in one of two ways. First, it can be formed by mixing/blending the unsaturated fatty acid (0 to 12.5 mol %), saturated fatty acid of chain length $C_{16}$ and up (50 to 87.5 mol %) and caustic (12.5 to 50 mol % of, for example NaOH or KOH) depending on extent of desired neutralization in the precursor matrix. In a second embodiment, it can be formed by mixing pre-formed soap with fatty acid so that no neutralization with caustic is required.

When a final bar comprising 40 to 88% by wt. fatty acid soap and/or fatty acid (at 50 mol % caustic, assuming made by neutralization method, there is 100% neutralization and bar is 100% soap; at less caustic, there is mixture of soap and fatty acid) of this precursor is blended/mixed with synthetic, water and filler, unexpectedly it has been found that the bar processes well (firmness of at least 100 kPa using cheese wire measurements) and has exceptionally good lather (bar lather assessment greater than 50 ml by prescribed methodology) as well as desirable potential mildness.

Thus, in one embodiment of the invention, a precursor bar/matrix formulation is made by formulating 0 to 12.5 mol % unsaturated fatty acid (e.g., oleic acid); 50 to 87.5 mol % saturated fatty acid of chain length $C_{15}$ to $C_{24}$, preferably $C_{16}$ to $C_{20}$; and 12.5 to 50 mol % caustic (depending on level of desired neutralization). The key is to form a precursor as "clean" as possible to the extent is has substantially no soaps or fatty acids (if undemeutralized) with chain length $C_{14}$ or below. When such precursor/matrix is later blended with other bar components, it will process well and, even in substantial absence of soluble fatty acid acid/soap (except for what may be brought in by other bar components other than those firming the precursor) unexpectedly provide excellent foaming.

In a second embodiment, the same "clean" precursor is formed but it is formed by blending pre-formed soap and free fatty acid (again with 0–12.5 mol % unsaturates and substantially no chain length components $C_{14}$ and below) without caustic to neutralize.

In effect, applicants have found a bar which can be made from non-nut oils (usually defining a mix of soluble, unsaturated; and insoluble longer chain saturated fatty acid) rather than mix of tallow and nut oils (where shorter chain saturates are normally found).

When short chain length soaps (which provide good user properties) are minimized, use of synthetic (e.g., anionic) is one way to make up for the loss in the bar user properties. According to the subject invention, however, there is minimized both the use of short chain soap/fatty acids and of synthetic surfactants (which may enhance other properties such as foam, but may also be harsh), while maintaining good user properties.

U.S. Pat. No. 5,387,362 to Tollens et. al discloses bars containing tailored mixtures of $Mg^{++}$, $Na^+$ and $K^+$ ions to react with lauric acid, select $C_{14}$–$C_{18}$ fatty acid and oleic acid. In the subject invention, lower chain length fatty acid (e.g. lauric) are minimized or substantially absent. Also, Tollens appears to be a pure soap bar composition while the bars of the subject invention require at least above 7% by wt. synthetic.

U.S. Pat. No. 5,262,079 to Kacher et al. discloses partially neutralizing mono carboxylic acids to form framed bars with high levels of anionic and nonionic firmness aids. The subject invention minimizes levels of synthetic (less than 25%, preferably less than 22%, more preferably 20% or less) and does not require firmness aids. It is also an extruded bar. The Kacher bars also must use above 15% water.

U.S. Pat. No. 6,121,216 to Narath et al. describes enhanced processing by minimizing soap level. The subject invention does not seek to minimize soap, but to offer beneficial soap blends.

BRIEF SUMMARY OF THE INVENTION

The present invention relates to predominantly soap/free fatty acid bars where a precursor bar with no more than certain level of unsaturated and substantially no fatty acid soaps or free fatty acids of chain length $C_{14}$ or below are used as a base or matrix for making high soap fatty acid, low synthetic bars which process well and foam remarkably well. The soap stock used to make the precursor bars is primarily from non-nut oil containing, for example, some soluble, unsaturated (e.g. oleic) and mostly insoluble, longer chain length fatty acids. By minimizing the level of unsaturates (e.g., oleic acid) and of lower chain saturates, applicants obtain bars that process well, have good lather and are acceptably mild. Use of low levels of appropriate synthetic surfactant helps assure that desirable properties such as lather and mildness are maintained. The bars can be made by neutralizing fatty acid with caustic (up to 100% can be neutralized); or by blending soap and fatty acid prior to surfactant addition.

Specifically, in one embodiment, the invention comprises a final bar composition comprising:

(1) a precursor bar composition comprising 40 to 88% by wt. final bar composition wherein said precursor is formed within a defined formulation range when the following mol % of components are mixed:
  (a) 0% to 12.5 mol % of unsaturated fatty acid;
  (b) 50 to 87.5 mol % fatty acid having chain length $C_{16}$ or greater, preferably $C_{16}$–$C_{22}$; and
  (c) 12.5 to 50 mol % caustic, (2) 7 to 25 wt. % synthetic surfactant;

(3) 5 to 15 wt. % water; and (4) 0 to 20 wt. % filler wherein said precursor bar composition is substantially free of soap or fatty acid having chain length $C_{14}$ or below.

wherein said final bar has substantially no soap or free fatty acid of chain length $C_{14}$ or below except for any which might be brought in by components other than those in the precursor bar composition; and wherein said final bar composition has lather of at least 50 ml as measured by a standard lather appraisal method (BLAM).

In this first embodiment, final balance of soap, free fatty acid (if any) and caustic (if any) is determined by how much fatty acid is neutralized by caustic.

In a second embodiment of the invention, the fatty acid soap and fatty acid used to make the precursor are formed by dispersing soap into fatty acid, or visa versa, prior to addition of surfactant and other bar ingredients rather than forming bar precursor by neutralization.

DETAILED DESCRIPTION OF THE INVENTION

Figure 1:
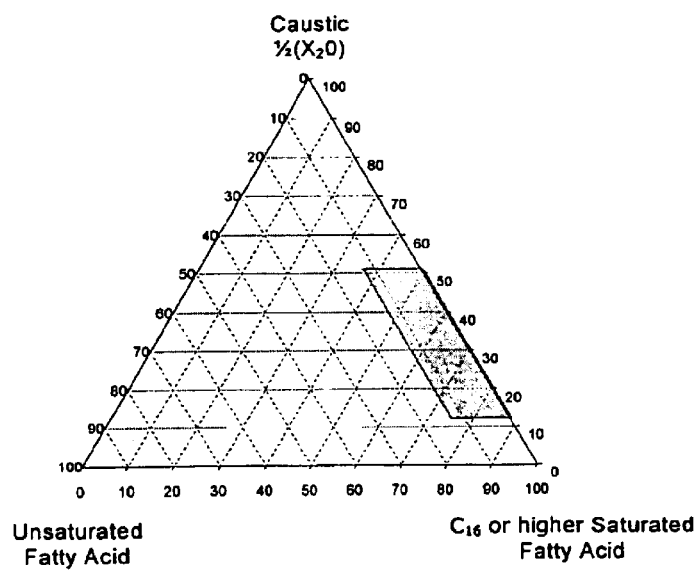
FIG. 1 shows a model of the range of mol % amounts (within shaded region) which may be used to form the bar precursor of the invention (when using neutralization embodiment). The precursor formed is substantially free of soaps/fatty acid of chain length $C_{14}$ and below and, when used to form final bar, will provide a bar which processes well and has unexpectedly good lather.

The present invention relates to predominantly soap/fatty acid, low synthetic (7 to 25% by wt) bar compositions which surprisingly both process and lather well. Specifically, by using a precursor bar composition with low level of unsaturates and substantially no component of chain length $C_{14}$ and below it has been found that it is possible to formulate final bars which surprisingly process and lather well.

More specifically, applicants have modeled a range in which mol % ratios of (1) long chain saturated fatty acid (e.g. palmitic/stearic), (2) unsaturated fatty acids (e.g. oleic); and (3) caustic (e.g. ½ ($Na_2O$)), when combined, form a matrix (see FIG. 1). When other bar ingredients are then mixed/blended with the precursor, a bar of optimal properties is formed.

Bar manufacture was accomplished by heating a mixer to about 80°–90° Celsius, adding the fatty acids (e.g., palmitic/stearic and oleic), followed by addition of the caustic to form precursor (precursor can also be formed by adding preformed soap and fatty acid, if any, without using caustic); and then followed by addition of surfactant and other bar materials. The mixture was dried to a target moisture and then cooled. The cooled material was then extruded via a bench top single screw plodder, made into billets and pressed. Lab evaluations, including lather volume, were then performed.

The mixer employed was a ploughshare mixer and batch preparation was as described: melt fatty acids, add caustic, add surfactant, then remove at the targeted moisture level. From the mixer the material was placed on a 3-roll mill in order to be quickly cooled. The subsequent ribbons were then perfumed and extruded on a 2 stage, single screw Mazonni plodder.

As noted, according to a second embodiment of the invention, fatty acid can be combined with previously formed soap (rather than forming soap via neutralization) prior to combination with synthetic surfactant and other materials.

More specifically, the final bar compositions of the invention comprise:

(1) 40% to 88% by wt. of a precursor or base bar composition which can be made either by combining fatty acid (having maximum amount of unsaturates and saturates substantially free of chain length $C_{14}$ and below) and caustic; or by blending preformed soap and fatty acids (also with maximum amount of unsaturates and substantially free if $C_{14}$ and below) without neutralizing.

(2) 7% to 25% by wt. preferably 10% to 22% by wt. synthetic surfactant;

(3) 5% to 15%, preferably 6% to 13% by wt. water, and (4) 0% to 20% by wt. filler (e.g., carbohydrates; waxes; emollients; salts such as carbonates, silicates; talc etc);

wherein (1) is substantially free of $C_{14}$ and below fatty acid soaps and free fatty acids; as is also the final bar except for any $C_{14}$ and below soaps/free fatty acids which may be brought in, for example, with synthetic surfactants. It is preferred, however, that final bar have less than 5%, preferably less than 3%, more preferably less than 2% and most preferably less than 1% by wt. $C_{14}$ and below.

The final bar also has lather of at least 50 ml measured by standard lather appraisal test.

When the precursor is made by neutralization, the mol % of starting reactants which are combined to form desired precursor which is low in unsaturates and substantially free of fatty acid soaps/free fatty acids of chain length $C_{14}$ and below is as follows (see FIG. 1):

(1) about 12.5 to 50 mol % caustic (50 mol % results in full neutralization);

(2) about 0 to 12.5 mol % unsaturated (e.g. oleic fatty acid), and (3) about 50 to 87.5 mol % long chain fatty acid of $C_{16}$ and above (e.g. palmitic/stearic)

Precursor bars/matrices formed within the preferred region may contain 0% to 65% by wt. free fatty acid (depending on level of neutralization); high levels of long chain ($C_{16}$ and above) fatty acid; and low levels of unsaturated fatty acid. Using underneutralization, it can be seen that these precursors can be used to form final bars with very high levels (up to 65%) of free fatty acid. Historically, superfatted bars contain 5% to 10% free fatty acid at most and even formulation based on synthetic with added free fatty acid (e.g. Dove®) have only about 25% free fatty acid. Thus, the amount used in the subject invention may be far higher than might previously have been believed possible.

Each of the components in the final bar composition is described in more detail below.

Base

With regard to the base or precursor bar composition, although certain molecules were used in the experimental models, it should be understood that the molecules used can be broader than those specifically exemplified.

Thus, for example, the unsaturated fatty acid may be oleic, linoleic or elaidic. The unsaturated fatty acid as noted, can be used at a level of 0 to 12.5 mol % as starting reactant during formation of bar precursor (e.g. when using neutralization methods). Even if blending preformed fatty acid soap and free fatty acid, unsaturates should comprise no more than 12.5 mol % of combined soap/fatty acid.

The long chain fatty acid is preferably a $C_{16}$–$C_{24}$, more preferably $C_{16}$ to $C_{22}$, even more preferably $C_{16}$ to $C_{20}$ fatty acids and mixture thereof and is used in an amount from about 50 to 87.5 mol % of starting fatty acid, if using neutralization or of total soap/fatty acid blend, if not using neutralization.

Finally caustic may be NaOH or KOH or any compound similar to these which will release a group IA metal such as, for example, caustic alcohol ($C_2HSONa$). The caustic may be used in an amount such that the fatty acid is underneutralized leaving a mixture of fatty acid soap and fatty acid. Generally, this is obtained by using 12.5 to under 50 mol % caustic. It should be understood that the caustic may fully neutralize fatty acid (e.g., 50 mol %) such that bar has only fatty acid soap. It is a benefit of the invention, however, to be able to obtain bars with much higher amount of free fatty add then would normally be able believed to be obtained thereby providing mildness benefits while still allowing good processing.

In another embodiment, a neutralization process need not be used, and the fatty acid may be combined with soap previously made prior to addition of surfactant and other bar materials to bar precursor.

The precursor bar may comprise 40 to 88% by wt., preferably 50 to 86% by wt., more preferably 55% to 85% by wt. of final bar (for example, if final bar has 5% water, 7% synthetic and no fillers, precursor bar would comprise 88% of precursor bar composition).

Surfactants

According to the invention, various surfactants can be used to blend/mix with the precursor bar composition.

The synthetic surfactants include anionic surfactants, nonionic surfactants, amphoteric/zwitterionic surfactants, cationic surfactants, etc. Such as are well known to the person skilled in the art. Among the many surfactants which may be used are those described in U.S. Pat. No. 3,723,325 to Parran Jr., et al. "Surface Active Agents and Detergents (Vol. I & II) by Schwartz, Perry and Berch, both of which are incorporated by reference into the subject application.

Examples of suitable anionic surfactants useful as auxiliary surfactants include: alkane and alkene sulfonates, alkyl sulfates, acyl isethionates, such as sodium cocoyl isethionate, alkyl glycerol ether sulfonates, fatty amidoethanolamide sulfosuccinates, acyl citrates and acyl taurates, alkyl sarcosinates, and alkyl amino carboxylates. Preferred alkyl or alkenyl groups have C12–18 chain lengths.

Examples of suitable nonionic surfactants include: ethoxylates (6–25 moles ethylene oxide) of long chain (12–22 carbon atoms) alcohol (ether ethoxylates) and fatty acids (ester ethoxylates); alkyl polyhydroxy amides such as alkyl glucamides; and alkyl polyglycosides.

Examples of suitable amphoteric surfactants include simple alkyl betaines, amido betaines, especially alkyl amidopropyl betaines, sulfo betaines, and alkyl amphoacetates.

The synthetic surfactant comprises 7 to 25% by wt., preferably 10% to 20% by wt. of final bar composition.

The final bars if the composition may comprise 5% to 15% by wt. preferably 6% to 13% water.

Finally, the final bars may contain 0 to 20% by wt. filler materials which may include anything from carboxylates (e.g. glucose, maltodextrins) to emollients (glycerin, propylene glycol), salts (e.g. carbonates, sulfates), water, starches and inorganic fillers (talc, mica). The fillers are not critical to the invention and merely illustrative of the many compounds which could be added to precursor and synthetic surfactant to create final bars.

Bars of the invention must have lather of at least 50 ml as measured by lather appraisal test defined herein.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight. Further, all ranges are to be understood to encompass both the ends of the ranges plus all numbers subsumed within the ranges.

EXAMPLES

Protocol

Bar Lather Volume Assessment (BLAM)

Principle

To determine the volume of lather which can be generated and collected from a given bar formulation under a strict regiment of washing.

Apparatus

Toilet bars 2 large sinks

Measuring funnel

The measuring funnel is constructed by fitting a 10½ inch diameter plastic funnel to a graduated cylinder which has had the bottom cleanly removed. Minimally the graduated cylinder should be 100 cc's. The fit between the funnel and the graduated cylinder should be snug and secure.

Procedure

Before evaluations proceed, place the measuring funnel into one of the sinks and fill the sink with water until the 0 cc mark is reached on the graduated cylinder.

i. Run the faucet in the second sink and set the temperature to 95° F. (35° C.).

ii. Holding the bar between both hands under running water, rotate the bar for ten (10) half turns.

iii. Remove hands and bar from under the running water.
iv. Rotate the bar fifteen (15) half turns.
v. Lay the bar aside.
vi. Work up lather for ten (10) seconds.
vii. Place funnel over hands.
viii. Lower hands and funnel into the first sink.
ix. Once hands are fully immersed, slide out from under funnel.
x. Lower the funnel to the bottom of the sink.
xi. Read the lather volume.
xii. Remove the funnel with lather from the first sink and rinse in the second sink.

The test should be performed on 2 bars of the same formulation, same batch etc. and the volume should be reported as an average of the 2 assessments.

Yield Stress Measure

The bars of the invention preferably have yield stress of at least 90 kPa, preferably 100 kPa measured using a cheese wire with a diameter of 0.5 millimeters and having a 200 gram weight attached.

Example 1

Establishing Prototype Model

Applicants sought to design a model soap base (defining ternary structuring system of the invention) to which additional surfactants could be added. The idea was to define a combination (or range) of long chain saturated to unsaturated soaps that could be acceptable to act as soap bases to which other surfactants could be formulated into. Having at least some free fatty acid was desirable to impart mildness.

Using phase factors, applicants established a model where the axes are scaled as mol %.

In general the following observation was made with regard to level of caustic used and resulting levels of soap and fatty acids:
  (1) using 50 mol % caustic results in full neutralization (all soap and no free fatty acid);
  (2) 37.5 mol % caustic results in 3:2 ratio of soap to fatty acid;
  (3) 25 mol % caustic results in 1:2 ratio of soap to fatty acid; and
  (4) 12.5 mol % caustic results in 1:6 ratio of soap to fatty acid.

Example 2

Bar Preparation

The mixer used in the preparation of the bar was a ploughshare mixer and a batch preparation was used. The procedure was to melt fatty acids (i.e., at temperature of about 65 to 105° C.), add caustic (to neutralize some or all free fatty acid), add surfactant, and remove at desired moisture. From the mixer, material was placed on 3-roll mill to quickly cool. Subsequent ribbons were extruded on a two-stage, single screw Mazzoni plodder.

Examples 3–30

Examples 3–30 below are all examples within scope of the invention wherein saturated longer chain length soaps/fatty acid are maximized; saturated, lower length soaps/fatty acids are minimized or absent, and level of unsaturates is always below a maximum mol % of fatty acid/caustic mixture (e.g. prior to saponification). Examples 3–30 are prepared via neutralization by caustic; Example 31 is prepared by adding soap into fatty acid before surfactant addition rather than by neutralization.

It will be noted that the bars process well (e.g., yield stress of at least 90, preferably at least 100 kPa as measured by cheese wire method defined in protocol) and have foam value of about 50 or more, preferably above 50, more preferably above 60.

It should be noted that a typical 82/18 soap bar lathers at a range of about 50–60 mol and Dove(C) lathers in a range of about 110–120 mol when measured by same method.

Examples are set forth below.

Example 3

| Molar Ratio of Soap/Fatty Acid | | |
| --- | --- | --- |
| $C_{16}/C_{18}$ | $C_{18:1}$ | NaOH |
| 75 | 0 | 25 |

| Nominal Composition | Weight % |
| --- | --- |
| Soap | 46 |
| Fatty Acid | 25 |
| Alpha-Step PC 48 (Stepan) (Surfactant)* | 20 |
| Water | 9 |

*Combination of sodium methyl-2 sulfo $C_{12}$–$C_{18}$ ester and disodium 2-sulfo $C_{12}$–$C_{18}$ fatty acid (i.e., a partially neutralized fatty acid methyl ester)

BLAM value: 73

This example shows soap/fatty acid for where large chain is 75% (molar ratio), unsaturates are absent, and fatty acid is underneutralized (25% NaOH). As seen, where long chain are maximized and both short chain and unsaturated minimized or absent, we obtain hard bars (processable) with good foaming.

Example 4

| Molar Ratio of Soap/Fatty Acid | | |
| --- | --- | --- |
| $C_{16}/C_{18}$ | $C_{18:1}$ | NaOH |
| 37.5 | 12.5 | 50 |

| Nominal Composition | Weight % |
| --- | --- |
| Soap | 71 |
| Fatty Acid | 0 |
| Alpha-Step PC 48 (Stepan) | 20 |
| Water | 9 |

BLAM value: 72

Here is an example of a bar with no free fatty acid at all (fully neutralized). Again, the bars are chain length specific (defined molar ranges for long chain length and unsaturates). Even excluding and/or minimizing the generally more solvent components such as unsaturates and short chain length, bars lather well (value of 72) as well as provide a good matrix for delivering surfactants.

Example 5

| Molar Ratio of Soap/Fatty Acid | | |
| --- | --- | --- |
| $C_{16}/C_{18}$ | $C_{18:1}$ | NaOH |
| 50 | 12.5 | 37.5 |

| Nominal Composition | Weight % |
| --- | --- |
| Soap | 43.9 |
| Fatty Acid | 27.1 |
| Alpha-Step PC 48 (Stepan) | 20 |
| Water | 9 |

BLAM value: 77

Here incomplete neutralization leaves 27.1% free fatty acid. Molar amounts of long chain ($C_{16}$–$C_{18}$) fatty acid/soap and unsaturates ($C_{18:1}$) are within defined limits. Lather volumes are good.

Example 6

| Molar Ratio of Soap/Fatty Acid | | |
| --- | --- | --- |
| $C_{16}/C_{18}$ | $C_{18:1}$ | NaOH |
| 75 | 0 | 25 |

| Nominal Composition | Weight % |
| --- | --- |
| Soap | 46 |
| Fatty Acid | 25 |
| Hostapon 85 | 20 |
| Water | 9 |

BLAM value: 100

Neutralization provides 46% soap and leaves 25% fatty acid. Molar ratios are within defined limits and lather is good.

Example 7

| Molar Ratio of Soap/Fatty Acid | | |
| --- | --- | --- |
| $C_{16}/C_{18}$ | $C_{18:1}$ | NaOH |
| 62.5 | 0 | 37.5 |

| Nominal Composition | Weight % |
| --- | --- |
| Soap | 43.9 |
| Fatty Acid | 27.1 |
| SASOLFIN 23S | 20 |
| Water | 9 |

BLAM value: 70

Same comments as previous example are relevant for this and remaining examples. Additional comments may be noted.

Example 8

| Molar Ratio of Soap/Fatty Acid | | |
| --- | --- | --- |
| $C_{16}/C_{18}$ | $C_{18:1}$ | NaOH |
| 75 | 0 | 25 |

| Nominal Composition | Weight % |
| --- | --- |
| Soap | 24.9 |
| Fatty Acid | 46.1 |
| SASOLFIN 23S | 20 |
| Water | 9 |

BLAM value: 92

Here it can be seen that 46.1% free fatty acid is in bar which is processable and lathers well.

Example 9

| Molar Ratio of Soap/Fatty Acid | | |
| --- | --- | --- |
| $C_{16}/C_{18}$ | $C_{18:1}$ | NaOH |
| 75 | 0 | 25 |

| Nominal Composition | Weight % |
| --- | --- |
| Soap | 22.6 |
| Fatty Acid | 41.9 |
| SASOLFIN 23S | 20 |
| Water | 9 |
| Glycerine | 5 |
| Perfume | 1.5 |

BLAM value: 127

Again an excellent value of 41.9% free fatty acid and is noted.

Example 10

| Molar Ratio of Soap/Fatty Acid | | |
| --- | --- | --- |
| $C_{16}/C_{18}$ | $C_{18:1}$ | NaOH |
| 50 | 12.5 | 37.5 |

| Nominal Composition | Weight % |
| --- | --- |
| Soap | 50.1 |
| Fatty Acid | 30.9 |
| SASOLFIN 23S | 10 |
| Water | 9 |

BLAM value: 73

Example 11

| Molar Ratio of Soap/Fatty Acid | | |
| --- | --- | --- |
| $C_{16}/C_{18}$ | $C_{18:1}$ | NaOH |
| 75 | 0 | 25 |

-continued

| Molar Ratio of Soap/Fatty Acid | |
|---|---|
| Nominal Composition | Weight % |
| Soap | 22.6 |
| Fatty Acid | 41.9 |
| Alpha-Step PC 48 (Stepan) | 10 |
| Hostapon 85 | 10 |
| Water | 9 |

BLAM value: 75

Example 12

| Molar Ratio of Soap/Fatty Acid | | |
|---|---|---|
| $C_{16}/C_{18}$ | $C_{18:1}$ | NaOH |
| 87.5 | 0 | 12.5 |

| Nominal Composition | Weight % |
|---|---|
| Soap | 10.8 |
| Fatty Acid | 60.2 |
| Alpha-Step PC 48 (Stepan) | 10 |
| Hostapon 85 | 10 |
| Water | 9 |

BLAM value: 62

Here there is free fatty acid of 60.2 wt. %

Example 13

| Molar Ratio of Soap/Fatty Acid | | |
|---|---|---|
| $C_{16}/C_{18}$ | $C_{18:1}$ | NaOH |
| 50 | 12.5 | 37.5 |

| Nominal Composition | Weight % |
|---|---|
| Soap | 50.1 |
| Fatty Acid | 30.9 |
| Alpha-Step PC 48 (Stepan) | 10 |
| Hostapon 85 | 10 |
| Water | 9 |

BLAM value: 75

Example 14

| Molar Ratio of Soap/Fatty Acid | | |
|---|---|---|
| $C_{16}/C_{18}$ | $C_{18:1}$ | KOH |
| 50 | 0 | 50 |

| Nominal Composition | Weight % |
|---|---|
| Soap | 71 |
| Fatty Acid | 0 |
| Alpha-Step PC 48 (Stepan) | 10 |
| Hostapon 85 | 10 |
| Water | 9 |

BLAM value: 70

Example 15

| Molar Ratio of Soap/Fatty Acid | | |
|---|---|---|
| $C_{16}/C_{18}$ | $C_{18:1}$ | KOH |
| 50 | 12.5 | 37.5 |

| Nominal Composition | Weight % |
|---|---|
| Soap | 49.6 |
| Fatty Acid | 30.6 |
| Alpha-Step PC 48 (Stepan) | 5 |
| Hostapon 85 | 5 |
| Water | 9 |

BLAM value: 52

Example 16

| Molar Ratio of Soap/Fatty Acid | | |
|---|---|---|
| $C_{16}/C_{18}$ | $C_{18:1}$ | NaOH |
| 87.5 | 0 | 12.5 |

| Nominal Composition | Weight % |
|---|---|
| Soap | 12 |
| Fatty Acid | 67 |
| Alpha-Step PC 48 (Stepan) | 5 |
| Hostapon 85 | 5 |
| Water | 9 |
| Sodium LAS | 2 |

BLAM value: 53

Values as high as 67% free fatty aid are noted in a processable bar.

Example 17

| Molar Ratio of Soap/Fatty Acid | | |
|---|---|---|
| $C_{16}/C_{18}$ | $C_{18:1}$ | NaOH |
| 75 | 0 | 25 |

| Nominal Composition | Weight % |
|---|---|
| Soap | 24.2 |
| Fatty Acid | 44.8 |
| Alpha-Step PC 48 (Stepan) | 10 |
| Hostapon 85 | 10 |
| Water | 9 |
| Sodium LAS | 2 |

BLAM value: 90

Example 18

| Molar Ratio of Soap/Fatty Acid | | |
|---|---|---|
| $C_{16}/C_{18}$ | $C_{18:1}$ | NaOH |
| 62.5 | 0 | 37.5 |

-continued

| Molar Ratio of Soap/Fatty Acid | |
|---|---|
| Nominal Composition | Weight % |
| Soap | 42.7 |
| Fatty Acid | 26.3 |
| Alpha-Step PC 48 (Stepan) | 10 |
| Hostapon 85 | 10 |
| Water | 9 |
| Sodium LAS | 2 |

BLAM value: 75

Example 19

| Molar Ratio of Soap/Fatty Acid | | |
|---|---|---|
| $C_{16}/C_{18}$ | $C_{18:1}$ | NaOH |
| 50 | 0 | 37.5 |
| Nominal Composition | | Weight % |
| Soap | | 42.7 |
| Fatty Acid | | 26.3 |
| Alpha-Step PC 48 (Stepan) | | 10 |
| Hostapon 85 | | 10 |
| Water | | 9 |
| Sodium LAS | | 2 |

BLAM value: 105

Example 20

| Molar Ratio of Soap/Fatty Acid | | |
|---|---|---|
| $C_{16}/C_{18}$ | $C_{18:1}$ | NaOH |
| 87.5 | 0 | 12.5 |
| Nominal Composition | | Weight % |
| Soap | | 10.5 |
| Fatty Acid | | 58.5 |
| Alpha-Step PC 48 (Stepan) | | 10 |
| Hostapon 85 | | 10 |
| Water | | 9 |
| Sodium LAS | | 2 |

BLAM value: 100

Example 21

| Molar Ratio of Soap/Fatty Acid | | |
|---|---|---|
| $C_{16}/C_{18}$ | $C_{18:1}$ | NaOH |
| 50 | 12.5 | 37.5 |
| Nominal Composition | | Weight % |
| Soap | | 36 |
| Fatty Acid | | 23 |
| Alpha-Step PC 48 (Stepan) | | 10 |
| Hostapon 85 | | 10 |
| Water | | 9 |

-continued

| Molar Ratio of Soap/Fatty Acid | |
|---|---|
| Sodium LAS | 2 |
| Calcium Carbonate | 10 |

BLAM value: 65

Example 22

| Molar Ratio of Soap/Fatty Acid | | |
|---|---|---|
| $C_{16}/C_{18}$ | $C_{18:1}$ | NaOH |
| 75 | 0 | 25 |
| Nominal Composition | | Weight % |
| Soap | | 38 |
| Fatty Acid | | 20 |
| Alpha-Step PC 48 (Stepan) | | 10 |
| Hostapon 85 | | 10 |
| Water | | 9 |
| Sodium LAS | | 2 |
| Calcium Carbonate | | 10 |

BLAM value: 85

Example 23

| Molar Ratio of Soap/Fatty Acid | | |
|---|---|---|
| $C_{16}/C_{18}$ | $C_{18:1}$ | NaOH |
| 75 | 0 | 25 |
| Nominal Composition | | Weight % |
| Soap | | 46 |
| Fatty Acid | | 25 |
| Alpha-Step PC 48 (Stepan) | | 7.5 |
| Hostapon 85 | | 7.5 |
| Water | | 9 |
| Sodium LAS | | 5 |

BLAM value: 55

Example 24

| Molar Ratio of Soap/Fatty Acid | | |
|---|---|---|
| $C_{16}/C_{18}$ | $C_{18:1}$ | 10:1 molar NaOH:KOH |
| 87.5 | 0 | 12.5 |
| Nominal Composition | | Weight % |
| Soap | | 8.6 |
| Fatty Acid | | 60.4 |
| Sodium Cocoyl Isethionate (e.g., Hostapon 85) | | 20 |
| Water | | 9 |
| Sodium LAS | | 2 |

BLAM value: 85

Example 25

| Molar Ratio of Soap/Fatty Acid | | |
|---|---|---|
| $C_{16}/C_{18}$ | $C_{18:1}$ | 10:1 molar NaOH:KOH |
| 50 | 12.5 | 37.5 |

| Nominal Composition | Weight % |
|---|---|
| Soap | 43 |
| Fatty Acid | 25 |
| Sodium Cocoyl Isethionate | 20 |
| Water | 10 |
| Sodium LAS | 2 |

BLAM value: 95

Example 26

| Molar Ratio of Soap/Fatty Acid | | |
|---|---|---|
| $C_{16}/C_{18}$ | $C_{18:1}$ | 10:1 molar NaOH:KOH |
| 62.5 | 12.5 | 25 |

| Nominal Composition | Weight % |
|---|---|
| Soap | 23 |
| Fatty Acid | 46 |
| Hostapon 85 | 20 |
| Water | 9 |
| Sodium LAS | 2 |

BLAM value: 60

Example 27

| Molar Ratio of Soap/Fatty Acid | | |
|---|---|---|
| $C_{16}/C_{18}$ | $C_{18:1}$ | NaOH |
| 51.6 | 0 | 48.6 |

| Nominal Composition | Weight % |
|---|---|
| Soap | 51.9 |
| Fatty Acid | 3.1 |
| Sodium cocoyl isethionate | 10 |
| Sodium laureth sulfate | 7 |
| Water | 9 |
| Lauryl sulfosuccinate | 7 |
| Glycerine | 5 |
| Cocamido propyl betaine | 4 |
| Polyethylene glycol | 3 |
| Perfume | 1 |

BLAM value: 60

Example 28

| Molar Ratio of Soap/Fatty Acid | | |
|---|---|---|
| $C_{16}/C_{18}$ | $C_{18:1}$ | NaOH |
| 75 | 0 | 25 |

| Nominal Composition | Weight % |
|---|---|
| Soap | 24.9 |
| Fatty Acid | 46.1 |
| Sodium N-cocoyl glycinate | 20 |
| Water | 9 |
| Perfume | 1 |

BLAM value: 95

Example 29

| Molar Ratio of Soap/Fatty Acid | | |
|---|---|---|
| $C_{16}/C_{18}$ | $C_{18:1}$ | NaOH |
| 75 | 0 | 25 |

| Nominal Composition | Weight % |
|---|---|
| Soap | 19.1 |
| Fatty Acid | 35.3 |
| Sodium cocoyl isethionate | 9.9 |
| Lauryl sulfosuccinate | 6.9 |
| Water | 8.9 |
| Sodium laureth sulfate | 6.9 |
| Glycerine | 4.9 |
| Cocamidopropyl betaine | 3.9 |
| Polyethylene glycol 1450 | 3 |
| Fragrance | 1.15 |

BLAM value: 112

Example 30

| Molar Ratio of Soap/Fatty Acid | | |
|---|---|---|
| $C_{16}/C_{18}$ | $C_{18:1}$ | NaOH |
| 50 | 12.5 | 37.5 |

| Nominal Composition | Weight % |
|---|---|
| Soap | 42.6 |
| Fatty Acid | 26.3 |
| Sodium N-cocoyl glycinate | 20 |
| Water | 6 |
| Talc | 3 |
| Titanium Dioxide | 0.4 |
| Perfume | 1.75 |

BLAM value: 93

All the previous examples were prepared via neutralizing distilled fatty acids. At least one example needs to be prepared where soap is dispersed into fatty acid prior to the surfactant addition as opposed to neutralization.

Example 31

| Molar Ratio of Soap/Fatty Acid | | |
|---|---|---|
| $C_{16}/C_{18}$ | $C_{18:1}$ | 10:1 molar NaOH:KOH |
| Nominal Composition | | Weight % |
| Sodium Stearate | | 25.14 |
| Palitic/Stearic Acid | | 45.86 |
| Alkyl Sulfate Sodium Salt | | 20 |
| Water | | 9 |
| Perfume | | 1.75 |

BLAM value: 115

Example 31 was not prepared via neutralization but by mixing powdered sodium stearate into molten fatty acid then following the rest of the procedure. The example demonstrates that it is the composition space which is unique and not simply the processing.

What is claimed is:

1. Bar composition comprising:
   (1) a precursor bar composition comprising 40 to 88% by wt. of final bar wherein said precursor is formed within a defined formulation range when the following mol % of components are mixed:
      a. 0 to 12.5 mol % unsaturated fatty acid
      b. about 50 to 87.5 mol % fatty acid having chain length $C_{16}$ or greater;
      c. about 12.5 to 50 mol % caustic;
   (2) about 7% to 25% by wt. final bar synthetic surfactant
   (3) about 5 to 15% by wt. final bar of water; and
   (4) about 0% to 20% by wt. final bar filler;
      wherein said precursor bar composition is substantially free of soap or fatty acid having chain length $C_{14}$ or below and said final bar has substantially no soap or free fatty acid of chain length $C_{14}$ or below except for any which may be brought in by components other than the precursor bar composition; and
      wherein said bar has lather of at least 50 ml as measured by standard lather appraisal test.

2. A composition according to claim 1, wherein fatty acid soap present in the final bar composition is formed from neutralization of fatty acid and caustic.

3. A composition according to claim 1 having yield stress value of at least 100 kPa.

4. A bar composition according to claim 1 wherein precursor bar comprises only
   (a) 0 to 12.5 mol % unsaturated fatty acid and
   (b) 50 to 87 mol % fatty acid of chain length $C_{16}$ or greater; and
      wherein precursor is formed from performed soap and fatty acid rather than b reaction of caustic and free fatty acid.

5. A composition according to claim 1 comprising 10% to 22% by wt. synthetic surfactant.

6. A composition according to claim 1 comprising 6 to 13% by wt. water.

* * * * *